(12) United States Patent
Rimke et al.

(10) Patent No.: US 8,482,738 B2
(45) Date of Patent: Jul. 9, 2013

(54) METHOD AND OPTICAL ARRANGEMENT FOR GENERATING A NONLINEAR OPTICAL SIGNAL ON A MATERIAL WHICH IS EXCITED BY AN EXCITATION FIELD, AND USE OF THE METHOD AND OF THE OPTICAL ARRANGEMENT

(75) Inventors: Ingo Rimke, Berlin (DE); Cees Otto, Hengelo (NL); Edlef Buttner, Berlin (DE); Hermann L. Offerhaus, Deventer (NL); Martin Jurna, Hengelo (NL)

(73) Assignee: APE Angewandte Physik and Electronik GmbH, Berlin (DE)

( * ) Notice: Subject to any disclaimer, the term of this patent is extended or adjusted under 35 U.S.C. 154(b) by 633 days.

(21) Appl. No.: 12/598,814

(22) PCT Filed: May 5, 2008

(86) PCT No.: PCT/EP2008/003582
§ 371 (c)(1),
(2), (4) Date: Mar. 25, 2010

(87) PCT Pub. No.: WO2008/135257
PCT Pub. Date: Nov. 13, 2008

(65) Prior Publication Data
US 2010/0177307 A1    Jul. 15, 2010

(30) Foreign Application Priority Data
May 4, 2007    (DE) .......................... 10 2007 021 378

(51) Int. Cl.
*G01B 9/02*    (2006.01)
(52) U.S. Cl.
USPC .......................................... 356/484; 356/450

(58) Field of Classification Search
USPC ...... 356/484, 450, 451, 300–334; 250/339.07
See application file for complete search history.

(56) References Cited

U.S. PATENT DOCUMENTS

| 3,381,233 A | 4/1968 | Seidel |
| 3,662,183 A | 5/1972 | Ashkin et al. |

(Continued)

FOREIGN PATENT DOCUMENTS

WO    2005116596    12/2005

OTHER PUBLICATIONS

Edlef Buttner et al., CARS imaging with a new, 532 nm synchronously pumped picosecond OPO, Progr. Biomed. Opt. Imaging Proc. SPIE, Progress in Biomedical Optics and Imaging—Proceedings of SPIE; Multiphoton Microscopy in the Biomedical Sciences VII 2007, vol. 6442, Feb. 10, 2007, XP002489933.

(Continued)

*Primary Examiner* — Gregory J Toatley
*Assistant Examiner* — Dominic J Bologna
(74) *Attorney, Agent, or Firm* — Bachman & LaPointe, P.C.

(57) ABSTRACT

A method of and an optical arrangement for generating a non-linear optical signal on a material excited by an excitation field, wherein with the excitation field coherent fields of first and second optical pulses of differing frequency are overlapped in the material in temporal and spatial relationship, wherein the first pulses of a first frequency are generated in a first beam of a first optical generator unit, and the second pulses of a second frequency are generated in a second beam of a second optical generator unit synchronously pumped by the first optical generator unit, wherein with the first pulses of the first frequency as a fundamental frequency pulses of a higher harmonic frequency thereof are generated and the second optical generator unit is pumped with the pulses of the higher harmonic frequency.

44 Claims, 4 Drawing Sheets

U.S. PATENT DOCUMENTS

| | | | |
|---|---|---|---|
| 4,193,690 A | 3/1980 | Levenson et al. | |
| 4,305,666 A | 12/1981 | Becherer et al. | |
| 4,405,237 A | 9/1983 | Manuccia et al. | |
| 4,512,660 A | 4/1985 | Goldberg | |
| 4,863,226 A | 9/1989 | Houpt et al. | |
| 4,905,244 A | 2/1990 | Wyeth et al. | |
| 5,034,613 A | 7/1991 | Denk et al. | |
| 5,117,126 A | 5/1992 | Geiger | |
| 5,365,366 A | 11/1994 | Kafka et al. | |
| 5,503,641 A | 4/1996 | Bakardjiev et al. | |
| 5,946,092 A | 8/1999 | DeFreez et al. | |
| 6,108,081 A | 8/2000 | Holtom et al. | |
| 6,403,966 B1 * | 6/2002 | Oka | 250/372 |
| 6,747,735 B2 | 6/2004 | Chen et al. | |
| 6,798,507 B2 | 9/2004 | Xie et al. | |
| 6,809,814 B2 | 10/2004 | Xie et al. | |
| 7,005,654 B2 | 2/2006 | Seyfried | |
| 7,027,468 B2 | 4/2006 | Krastev et al. | |
| 7,092,086 B2 | 8/2006 | Knebel | |
| 7,388,668 B2 * | 6/2008 | Potma et al. | 356/451 |
| 7,738,111 B2 * | 6/2010 | Bennett | 356/484 |

OTHER PUBLICATIONS

M. Jurna et al., Noncritical phase-matched lithium triborate optical parametric oscillator for high resolution coherent anti-Stokes Raman scattering spectroscopy and microscopy, Applied Physics Letters, AIP, American Institute of Physics, Melville, NY, vol. 89, No. 25, Dec. 21, 2006, XP012087711.

Eric O. Potma et al., High Repetition rate femtosecond lightsource for CARS microscopy, Conference Digest 2000 Conference on Lasers and Electro-Optics Europe (Cat. No. 00TH8505) IEEE Piscataway, NJ, 2000, XP002489934.

M. Greve et al., Gated heterodyne coherent anti-Stokes Raman scattering for high-contrast vibrational imaging, Proceedings of the SPIE, The International Society for Optical Engineering SPIE-Int. Soc. Opt. Eng. USA, vol. 5856, No. 1, 2005, XP002489935.

M. Greve et al., High-contrast chemical imaging with gated heterodyne coherent anti-Stokes Raman scattering microscopy, Applied Physics B (Lasers and Optics), Springer-Verlag Germany, vol. B81, No. 7, Nov. 2005, XP002489936.

M. Jurna et al., Shot noise limited heterodyne detection of CARS Signals, Feb. 23, 2007.

E. O. Potma et al., Heterodyne coherent anti-Stokes Raman scattering (CARS) imaging, Optics Letters, vol. 31, No. 2, Jan. 15, 2006.

B. Vacano et al., Highly sensitive single-beam heterodyne coherent anti-Stokes Raman scattering, Optics Letters, vol. 31, No. 16, Aug. 15, 2006.

F. Ganikhanov et al., High-sensitivity vibrational imaging with frequency modulation coherent anti-Stokes Raman scattering (FM CARS) microscopy, Optics Letters, vol. 31, No. 12, Jun. 15, 2006.

E. R. Andresen, Picosecond anti-Stokes generation in a photonic-crystal fiber for interferometric CARS microscopy, Optics Express, vol. 14, No. 16, Aug. 7, 2006.

F. Ganikhanov et al., Broadly tunable dual-wavelength light source for coherent anti-Stokes Raman scattering microscopy, Optics Letters, vol. 31, No. 9, May 1, 2006.

\* cited by examiner

METHOD AND OPTICAL ARRANGEMENT FOR GENERATING A NONLINEAR OPTICAL SIGNAL ON A MATERIAL WHICH IS EXCITED BY AN EXCITATION FIELD, AND USE OF THE METHOD AND OF THE OPTICAL ARRANGEMENT

FIELD OF THE INVENTION

The invention concerns a method of generating a non-linear optical signal on a material excited by an excitation field, wherein with the excitation field coherent fields of first and second optical pulses of differing frequency are overlapped in the material in temporal and spatial relationship, wherein the first pulses of a first frequency are generated in a first beam of a first optical generator unit, and the second pulses of a second frequency are generated in a second beam of a second optical generator unit synchronously pumped by the first optical generator unit, wherein with the first pulses of the first frequency as a fundamental frequency pulses of a higher harmonic frequency thereof are generated (SHG) and the second optical generator unit is pumped with the pulses of the higher harmonic frequency. The invention further concerns an optical arrangement for generating a non-linear optical signal on a material excited by an excitation field, wherein with the excitation field coherent fields of optical pulses of differing frequency are overlapped in the material in temporal and spatial relationship. The invention also concerns a use of the method and of the optical arrangement.

BACKGROUND OF THE INVENTION

The use of an aforementioned CARS method and/or CARS optical arrangement has become established in particular in the region of investigating internal vibronic structures of molecules, wherein for example a non-linear optical signal in the form of a CARS signal (Coherent Anti-Stokes Raman Spectroscopy Signal) can be produced on a material. By way of example the article by F Ganikhanov et al, in: Optics Letters, Vol 31 (12), pages 1872-1874 (2006) describes a high-sensitivity CARS structure which operates with two lasers and a resonator-internal frequency-doubled OPO. That permits marker-free identification of a molecule. Thus for example fluorescence spectroscopy markered species as possible alternatives but in particular in the biological or foodstuffs sector are found to be not application-related by virtue of the frequently excessively low marker action and possibly toxic action of the markers. The method and the apparatus set forth in the opening part of this specification thus form a promising and viable option if it is possible to reduce the complexity of existing systems and at the same time enhance the sensitivity thereof. The resonant elevation inherent in the CARS process makes it more sensitive than Raman spectroscopy and in comparison with infrared spectroscopy the use of shorter wavelengths in the present case permits a higher level of spatial resolution in the region of microscopy. For that reason amongst others the use of a method as set forth in the opening part of this specification and the above-mentioned apparatus in the context of CARS spectroscopy and microscopy has acquired a not inconsiderable significance. The implementation thereof on a larger, application-related or industrial scale has hitherto been limited by virtue of the still comparatively high degree of complexity of the systems required for same and the comparatively low yield of the non-linear optical signal which is generated in the material by means of an available interaction which is non-linear to a high degree. Those problems arise in particular in relation to materials in which the substance to be investigated is present in a comparatively low concentration.

Thus the publication by E O Potma et al in Opt Lett 31, No 2, pages 241 through 243, 14 Jan. 1006 'Heterodyne coherent anti-Stokes Raman scattering (CARS) imaging' and the publication by E R Andresen in Opt Expr Vol 14 (16), pages 7246-7251 (2006) 'Picosecond anti-Stokes generation in a photonic-crystal fiber for interferometric CARS microscopy' basically propose developing a multi-beam arrangement as referred to in the opening part of this specification for a method and an optical structure for generating the non-linear optical signal by the use of an optical parametric oscillator and a heterodyne detection system. For that purpose E O Potma et al propose, for a CARS arrangement, using a pulse of a signal beam, which is frequency-doubled in the resonator of the optical parametric oscillator (OPO), as a high-frequency excitation field, and using a laser pulse generated by a pump laser for the OPO as a low-frequency excitation field, in the CARS terminology as the Stokes beam. To implement a heterodyne detection system an additional CARS structure is made available in a defined manner in the CARS structure, in the context of a Mach-Zehnder interferometer, wherein one of the arms of the interferometer has a cell of deuterated dimethylsulfoxide (d-DMSO) for generating a strong non-resonant signal at a—in the CARS terminology—anti-Stokes frequency, which serves as a so-called 'local oscillator' in accordance with the heterodyne detection system. Such a structure is comparatively complex and complicated to handle although the proposed heterodyne detection system is basically suitable for increasing a level of sensitivity of the aforementioned method and the aforementioned apparatus.

In the publication by E R Andresen et al once again a signal output of an OPO synchronously pumped to a laser frequency serves as a high-frequency pump pulse for the excitation field for generating a CARS signal while a laser pulse at the laser frequency serves as a low-frequency Stokes pulse for forming the excitation field. Pump and Stokes pulses are fed to a photonic-crystal glass fiber (PCF) to represent a local oscillator field in the anti-Stokes pulse in accordance with the heterodyne detection system for CARS. The dispersion and transit time properties linked thereto concerning the anti-Stokes pulse give rise to additional problems which make the method described therein and the structure described therein still worthy of improvement.

The publication 'CARS imaging with a new 532 nm synchronously pumped picosecond OPO' by Bfttner et al, which appeared in Proc of SPIE Conf Multiphoton Microscopy in the Biomedical Sciences VII (21-23 Jan. 2007), edited by A Periasamy et al, SPIE, 2007 Vol 6442, pages 64420C-1 through 64420C-8), basically describes an advantageous optical CARS structure with an OPO, which is pumped with a frequency-doubled, mode-coupled Nd: VAN laser. There a signal beam of the OPO is used together with a part of the fundamental of the pump laser as a pump and Stokes beam on the implementation of a CARS excitation field.

SUMMARY OF THE INVENTION

A comparatively high-power and compact approach for further improving a method as set forth in the opening part of this specification and an optical arrangement as set forth in the opening part of this specification would be desirable, in which respect in addition the aim is to provide an advantageous option of heterodyne detection for the non-linear optical signal.

It is at this juncture that the invention comes in, the object thereof being to provide a method and an optical arrangement of the kind set forth in the opening part of this specification, which can be used comparatively simply and/or compactly in terms of structure and in that respect nonetheless of comparatively high power for the generation of the non-linear optical signal, in particular comparatively sensitively for the detection of the non-linear optical signal.

In regard to the method that object is attained by the invention by means of a method of the kind set forth in the opening part of this specification, in which it is provided in accordance with the invention that the second optical generator unit as an optical parametric generator unit generates pulses of an idler frequency in an idler beam for providing the second pulses of the second frequency in the second beam, wherein the second frequency is smaller than the first frequency, and the second optical generator unit generates pulses of a signal frequency in a signal beam, wherein the second frequency is smaller than the signal frequency.

The invention is based on the consideration that in a distinction in relation to the state of the art, it is possible to achieve particularly high-power excitation of a material in the context of an excitation field which is formed by means of a first pulse, for example a pump pulse of higher frequency generated by a pump laser, and a second pulse, for example an idler pulse of lower frequency generated by an optical parametric oscillator. In other words the fundamental frequency of the preferably laser serves as a pump frequency (first pulse) in accordance with a CARS terminology while the idler frequency, preferably of the OPO, serves as a Stokes frequency (second pulse). The invention realised that this kind of generation of an excitation field with the second pulse is possible if in accordance with the concept of the invention the optical parametric generator unit is pumped on the higher harmonic frequency formed by multiplication of the fundamental frequency.

In addition the invention realised that the combination of the first fundamental frequency and the second idler frequency in the excitation field leads to a non-linear signal, for example a CARS signal, on the frequency $$\Omega_{CARS} = 2\Omega_{pump} - \Omega_{Idler}$$

which corresponds to the signal frequency $\Omega_{signal}$ of the signal pulse generated for example by the parametric oscillator, in a signal beam. In that respect the present method of generating the non-linear optical signal for the first time offers a particularly good and high-power possible way of using the signal pulse generated by the optical parametric generator unit in the context of a heterodyne detection system for the non-linear optical signal. The method and an optical arrangement suitable for same are found to be comparatively compact and simple to handle in comparison with previous concepts.

Accordingly the concept of the invention leads to an optical arrangement of the kind set forth in the opening part of this specification, which is suitable in particular for carrying out the method according to the concept of the invention. In accordance with the invention the optical arrangement further comprises:
  a first optical generator unit for generating the first pulses of a first frequency in a first beam,
  a means for generating pulses of a higher harmonic frequency with the pulses of the first frequency as a fundamental frequency, a second optical generator unit which is pumpable by the first optical generator unit synchronously with the pulses of the higher harmonic frequency and which is in the form of an optical parametric generator unit for generating pulses of an idler frequency in an idler beam as second pulses in the second beam at a second frequency and for generating pulses of a signal frequency in a signal beam, wherein the second frequency is smaller than the first frequency and smaller than the signal frequency, and
  beam guide means for temporal and local overlapping of a first pulse of the first beam and a second pulse of the idler beam.

The expression an optical parametric generator unit is basically to be interpreted as meaning any optical generator unit which is adapted by way of a parametric process of frequency splitting of the pump frequency to generate an idler frequency and a signal frequency, the sum of the idler frequency and the signal frequency giving the pump frequency.

Basically instead of an OPO it is also possible to use an optical parametric generator (OPG)—that is to say an OPO without resonator—or an optical parametric amplifier with or without resonator (OPA). The generator units are preferably in the form of picosecond (ps) versions, possibly also in the form of a femtosecond (fs) version. An OPO or OPG or OPA preferably uses a KTP crystal as the non-linear crystal. The use of ps-pulses allows spectrally targeted investigations of specific junctions (single-line) while fs-pulses permit frequentially wide applications, for example with frequency modulation or the like (multi-line).

The concept of the invention advantageously uses the fact that the sum of idler frequency and signal frequency corresponds to the higher harmonic frequency, in particular the second harmonic frequency. That permits the option of particularly noise-free detection of the non-linear optical signal in the context of a heterodyne detection system.

The concept of the invention leads to a particularly preferred use of the method and/or the optical arrangement for the chemically selective investigation of chemical substances and/or biological substances, in particular in the foodstuffs sector. The use manages without invasive markers or the like and in addition affords the possibility of enhanced sensitivity in comparison with the state of the art. The invention further concerns the use of the method or the optical arrangement according to the concept of the invention for the investigation of vibronic states in a molecule. It has been found that in the context of the use investigation of substances even with a sub-milli-molar concentration of a molecule is possible.

According to the invention the method and/or the optical arrangement according to the concept of the invention is used for microscopy and/or spectroscopy, in particular CARS microscopy and/or CARS spectroscopy. According to the invention there is provided a use in frequency metrology, in particular with phase-stabilised optical generator units.

The invention realised for the first time that the combination of the fundamental frequency of the first optical generator unit (for example laser) and the idler frequency of the second optical generator unit (for example OPO) is particularly attractive for generation of the non-linear signal because in that way the spacing between the anti-Stokes frequency and the pump frequency is comparatively great; in other words the anti-Stokes region is completely free from any frequency overlap in respect of the exciting pulses. That is not the case for excitation schemata which use the signal frequency of the second optical generator unit as a pump frequency and the fundamental frequency of the first optical generator unit as an anti-Stokes frequency—there an overlap is to be expected with the signal region in the course of sampling of a CARS spectrum, which makes it necessary to use limiting filters which possibly give rise to problems. That measure is avoided in accordance with the concept of the invention. Rather it is possible to detect wider CARS spectra (for example markedly more than 80 wave numbers, for example in the case of a plurality of Raman resonances or hyperspectra even in the area of the temperature bandwidth).

Besides the above-mentioned advantages it has also been found that dispersion problems and temporal jitter problems as well as pulse guidance problems as in the comparatively complex structures of the state of the art are advantageously avoided by the concept of the invention. In addition the pulse widths which can be achieved—in temporal terms and in the frequency domain—can be optimised reliably and in a superior fashion. The cascaded 'color' generation originating from a single mother source—the first optical generator unit—in accordance with the invention makes the concept thereof particularly simple, compact and user-friendly in comparison with all known systems. The concept of the invention affords the possibility of particularly effective and noise-free heterodyne detection which in a manner still to be described allows the detection of weak-signal, non-linear optical signals.

Advantageous developments are recited in the appendant claims and set forth in detail advantageous possible ways of implementing the above-discussed concept in accordance with the object of the invention and in respect of further advantages.

In accordance with a particularly preferred development it was realised that an optical phase position is defined between a pulse of the signal beam and the non-linear optical signal. Admittedly a phase position between a pulse of the first beam and a pulse of the second beam is not in direct relationship with each other, that is to say the phase positions of the pulses for representation of the excitation field do not involve a direct phase relationship with each other, but the outgoing phase of the non-linear optical signal is phase-locked in relation to the phase of the pulse of the signal frequency in the signal beam which is generated by the optical parametric oscillator. In other words the phase of mutually associated pulses of a signal beam and an idler beam per se are free. The sum thereof however is phase-locked relative to the phase of the pump laser. That fact of phase retention in accordance with a particularly preferred development of the invention allows heterodyne detection of the non-linear optical signal insofar as it is overlapped with the signal beam in interfering relationship. Overall that fact can be used to boost a non-linear signal by an interferometric procedure.

Preferably the signal frequency and the frequency of the non-linear optical signal coincide in order of magnitude—in accordance with a development for heterodyne detection of the non-linear signal a frequency and/or phase of the non-linear optical signal is altered relative to the signal frequency and/or phase and the non-linear optical signal is detected as a time-dependent interfering signal.

Preferably a frequency and/or phase of the non-linear optical signal is altered relative to the signal frequency by the first frequency and/or phase being altered. That has the advantage that the first frequency and/or phase—namely the fundamental frequency and/or phase of the first optical oscillator, for example a laser, is altered, which in accordance with the method, for example for adaptation of a frequency of the excitation field to a given material, is no longer necessarily tuned. In other words this involves comparatively stable conditions for the defined frequency and/or phase alteration in respect of heterodyne detection. Preferably the first beam is acousto-optically modulated, which desirably leads to a suitable frequency and/or phase alteration—basically any kind of optical frequency and/or phase modulator is suitable for that purpose.

In particular the non-linear optical signal is formed in the form of a CARS signal, that is to say with a frequency corresponding to double the first frequency minus the idler frequency. In that way in accordance with the present development it is for the first time possible in the context of a multi-beam arrangement with implementation of an optical parametric oscillator for heterodyne detection of a CARS signal, to use each of the frequencies generated by the generator units for the CARS frequencies (pump, Stokes, anti-Stokes), in which respect for the first time the phase relationship of the signal of the optical parametric oscillator relative to the non-linear optical signal is put to use. In accordance with the concept of the invention that is made possible by pumping of the second parametric optical generator unit on a higher harmonic of a first optical generator unit, as described hereinbefore.

In accordance with a particularly preferred development the first and second beams are collinearly overlapped to form the excitation field. Preferably in a first variant the signal beam is not passed on to the material. In particular the signal beam for heterodyne detection is collinearly overlapped with the non-linear optical signal, for example in a suitable detector. A high-linear arrangement is comparatively simple to achieve, but in principle any kind of an overlap sufficient for detection is appropriate.

In a second variant the signal beam can also be collinearly overlapped in the material with the first and second beams. In accordance with a first modification for that purpose the intensity of the signal beam can be selected to be low in such a way that a strength of the non-linear optical signal is uninfluenced by the signal beam. In accordance with a second modification the intensity of the signal beam can be selected to be high in such a way that a strength of the non-linear optical signal rises with the intensity of the signal beam. In accordance with the development therefore the signal beam can be used as part of the excitation field to stimulate the generation of the non-linear optical signal. Both in that variant and also in the previously mentioned variant, a resonant and a non-resonant signal component of the non-linear signal can be separated in the context of heterodyne detection by suitable analysis of the signal. The stimulated non-linear optical signal can reach very much higher levels than the amplitude of a straightforward difference signal—the latter in the case of a signal beam in front of the material at lower intensity or a signal beam behind the material. The strong-intensity use of the signal beam in the material, in accordance with the realisation of this development, also stimulatingly alters the non-linear interaction in the material in such a way that for example one of the interacting junctions of a given excitation is driven. Preferably pump, idler and signal beams of practically equal intensity are applied to the material. That kind of 'stimulated' CARS application, in which the CARS field is stimulatingly 'sown' affords a surprisingly effective and completely novel option in spectroscopy and/or microscopy.

Furthermore it has proven to be advantageous, as required, to select certain polarisation arrangements for an excitation field to be able to investigate certain material properties. While otherwise the fields of the first and second beams can be copolarised a non-copolarised, for example cross-polarised, arrangement affords the advantage that a non-resonant part of a non-linear signal can be suppressed so that only the resonant components interfere and are detected. In addition the polarisation of the fields of the first and second beams can be so selected that the excitation field is circularly or elliptically polarised. That has proven itself in particular for investigating birefringence or handedness/chirality of molecules, in which case a corresponding molecule state can be checked by adapted polarisation of the excitation field.

Advantageous developments of the invention in regard to the optical arrangement are to be found in the appendant claims and set forth in detail advantageous possible ways of implementing the above-discussed concept in accordance with the object of the invention and in respect of further advantages. Thus the development of the apparatus has proven to be particularly advantageous for detection of the non-linear optical signal by heterodyne interfering overlap with a further beam. Preferably there is provided a means for altering the frequency of the non-linear optical signal relative to the signal frequency of the signal beam and a detector and further beam guide means for heterodyne interfering overlap of the non-linear optical signal with the signal beam in the detector.

The first optical oscillator is preferably in the form of a laser, for example an Nd:YAG laser or titanium sapphire laser.

In accordance with a particularly preferred development the apparatus provides means for generating a higher harmonic frequency in the form of a frequency doubler. In particular that can be implemented by the arrangement of one or more non-linear crystals in a suitable housing provided with adjusting mechanisms and/or an additional resonator.

In a variant, additionally or alternatively, the means for generating a higher harmonic frequency can be arranged between the first optical oscillator and the second optical oscillator or in another variant, additionally or alternatively, the means for generating a higher harmonic frequency can be formed in the resonator of the first optical oscillator. For example there can be provided a laser which in frequency doubling effected in the laser resonator, generates both the first frequency as a fundamental frequency and also a higher harmonic of the fundamental frequency, in particular the double harmonic of the fundamental frequency.

In principle a means for altering the frequency and/or the phase of the non-linear optical signal relative to the frequency and/or the phase of the signal beam, additionally or alternatively to the means for altering the fundamental frequency/phase in the first beam, can also be arranged for altering the idler frequency/phase in the idler beam and/or for altering the signal frequency/phase in the signal beam. That can be for example an acousto-optical modulator—in principle any suitable choice of a frequency and/or phase modulator is possible.

A detector is preferably in the form of a photomultiplier, a photodiode or an avalanche diode. It has surprisingly been found that the noise characteristics, in particular for the region of heterodyne detection, are particularly advantageous in the case of a photodiode. Admittedly the use of a photomultiplier is in principle to be recommended in relation to low signal levels, but even for low signal levels, in particular in accordance with th above-described development of stimulated generation of the non-linear signal, there is a possible way of raising the signal level of the non-linear signal and thereby permitting the use of a lower-noise photodiode, in particular with a resistance above 1 MΩ, preferably up to or above 10 MΩ. In that way shot noise limited heterodyne detection of a non-linear signal, in particular a CARS signal, becomes possible for the first time.

Embodiments by way of example of the invention are now described with reference to the drawing in comparison with the state of the art which is in part also illustrated. This is intended to represent the embodiments not necessarily true to scale, but rather the drawing, where appropriate for description, is in diagrammatic and/or slightly distorted form. In regard to supplements to the teachings which can be directly seen from the drawing attention is directed to the pertinent state of the art. In that respect it is to be borne in mind that many different modifications and alterations concerning the form and the detail of an embodiment can be effected without departing from the general idea of the invention. The features of the invention disclosed in the description, the drawing and the claims can be essential for the development of the invention both individually and also in any combination. In addition all combinations of at least two of the features disclosed in the description, drawing and/or claims fall within the scope of the invention. The general idea of the invention is not limited to the exact form or detail of the preferred embodiments described and illustrated hereinafter or limited to a subject-matter which would be restricted in comparison with the subject-matter claimed in the claims. In regard to specified dimensional ranges values within the stated limits are also to be disclosed as limit values and can be used as desired and can be claimed.

DETAILED DESCRIPTION

With reference to the drawing the use of an optical arrangement 10 and of the method in accordance with the concept of the invention for CARS (coherent anti-Stokes Raman scattering) spectroscopy is described here as a particularly preferred embodiment. It is demonstrated that it is possible for even weak CARS signals of hitherto unattainable molecules below a milli-molar concentration to be detected in the region of the shot noise limit in the context of a particularly compact optical structure, wherein the phase coherence of the CARS process is used for heterodyne detection. The structure of the optical arrangement 10 and the method are found to be superior in respect of their compactness and their noise characteristics respectively, in relation to previously known concepts in the state of the art.

Figure 1:
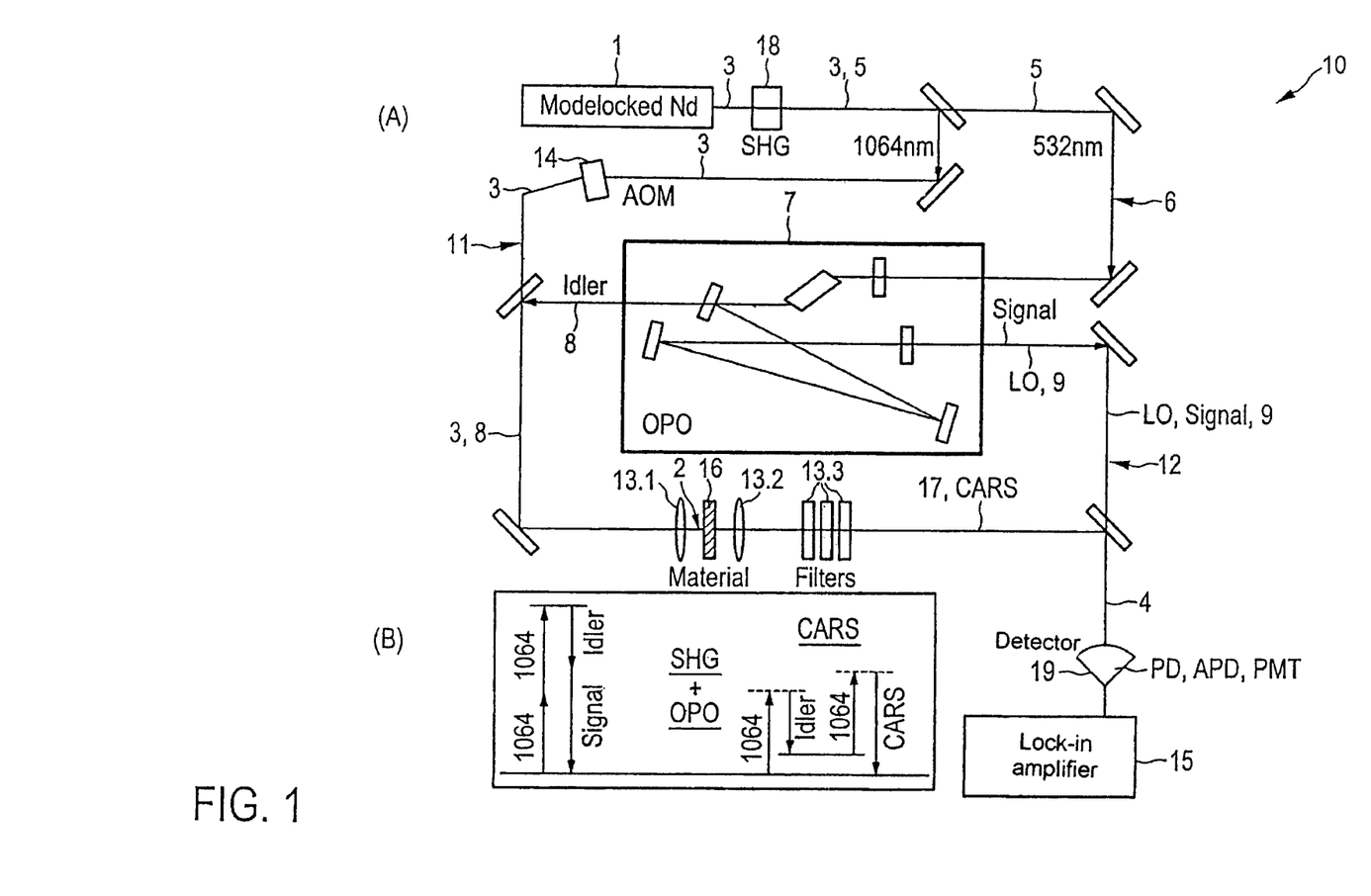
FIG. 1 in view A shows a diagrammatic representation of an optical structure for generation and heterodyne detection of a CARS signal with an optical parametric oscillator synchronously pumped on the second harmonic of a fundamental laser frequency, wherein the fundamental laser frequency and the idler frequency are used to generate an excitation signal for a material and the signal frequency is used for heterodyne detection of the CARS signal; view B shows an associated energy diagram of the frequencies involved and the occurrence of the CARS signal in the energy diagram for a non-linear third-order process.

Although in the present case the input wavelengths which generate the CARS signals—namely a fundamental laser frequency and an idler frequency—do not have a direct phase relationship, nonetheless the output wavelength of the CARS signals is phase-locked in relation to a wavelength of the OPO signal which is generated simultaneously with the idler signal in the optical parametric oscillator of the FIG. 1 structure in order to generate a suitable so-called local oscillator field for heterodyne detection of the CARS signal. Analysis of the noise properties of the detection diagram reveals a niche which allows the CARS signal to be detected at the shot noise limit. Additional measurements with attenuation of the CARS signal show that detection of the CARS signal level is markedly below the detector noise level (dark level) and the current detector limits. The structure of the optical arrangement 10 is inherently free from a temporal jitter in respect of the correlated pulses and uses any of the wavelength generated in accordance with the structure for generation and detection of the CARS signal.

FIG. 1 shows in that respect the phase-retaining non-linear chain of the structure of the optical arrangement 10 as a particularly preferred embodiment of an apparatus for generating and detecting the non-linear optical signal 17 in the form of the CARS signal. It has a first optical generator unit 1 in the form of an oscillator for generating pulses of a first frequency in a first beam 3. The first optical oscillator is for that purpose in the form of a passively mode-locked Nd:YAG laser for the generation of pulses of a pulse width of about 15 ps at a repetition rate near 80 MHz. The central wavelength of the pulses is at 1064 nm and that wavelength which predetermines a fundamental frequency is partially used in a frequency doubler 18 which in the present case is provided externally in the beam 3 for the generation of pulses of a 12 ps width at 532 nm. The frequency-doubled part of the beam 3 is fed in the form of a phase-coherent pump beam 5 for pumping a second optical generator unit 7 in the form of an optical parametric oscillator to the input of the optical parametric oscillator by way of suitable mirrors in a pump branch 6 of the suitably designed beam guide arrangement. Phase coherence is afforded by addition of the phases of the two photons forming the second harmonic frequency (532 nm). In an embodiment which in the present case is diagrammatically shown in FIG. 1, the optical parametric oscillator which is thus synchronously pumped at 532 nm generates pulse pairs of a pulse width of about 6.5 ps on the one hand with a signal wavelength of a signal beam 9 and on the other hand an idler wavelength of an idler beam 8. The phases of the correlated pulses of the signal beam 9 and the idler beam 8 are per se free, but addition is locked to the phase of the pump beam 3. That freedom of the phase of the signal beam 9 ensures that the signal supported in the resonator does not involve a phase limitation and thus permits smooth operation of the optical parametric oscillator (GPO). The wavelength of the idler beam 8 is combined in the branch 11 of the beam guide means, that carries the first beam 8, with the 1064 nm of the first beam 3 to produce an excitation field 2 and a CARS signal at a frequency of:

$$\Omega_{CARS} = 2\Omega_{pump} - \Omega_{Stokes}$$

wherein the 1064 nm acts as a pump frequency and the frequency of the idler beam 8 acts as a Stokes wavelength.

The CARS (or anti-Stokes) wavelengths, as can be seen from view B in FIG. 1, correspond to the wavelength of the signal beam 9 of the OPO. In addition the phase of the resonant CARS signal is determined practically in the same manner as the phase of the signal beam 9 of the OPO ($2 \times \text{phase}_{1064} - \text{phase}_{Idler} + \text{phase}_{Chi\,(3)}$), wherein the last term is a constant phase of the non-linear response Chi (3) at a given wavelength. Phase maintenance signifies that the signal wavelength can interfere with the CARS signal in a predictable fashion in the interference beam 4 of the second branch 12 of the beam guide arrangement and can thus be used for interferometric amplification.

The interference of the local oscillator field (LO, OPO-signal wavelength 9) with the CARS signal (CARS) leads to a total intensity on the detector of:

$$I_{detector} = LO + CARS + 2 \times \sqrt{(LO \cdot CARS)},$$

wherein $HCARS = 2 \times \sqrt{(LO \cdot CARS)}$, wherein LO and CARS represent intensities. HCARS relates to the heterodyne CARS power. That interference term scales with the root of the power of the LO field and the interferometric amplification can be defined as $HCARS/CARS = 2 \times \sqrt{(LO/CARS)}$. The noise of the optical signal is determined by the shot noise in the CARS signal itself and the shot noise which is introduced by the local oscillator signal, that is to say the OPO signal 9. The introduced shot noise is the dominant part of the two (because LO is very much greater than CARS) and scales with the root of LO, similarly to the interference term and the interferometric amplification. The interferometric amplification can therefore be used to lift the signal above the detector noise without degrading the original signal-to-noise ratio as long as the local oscillator field LO is the dominant term for the shot noise. To avoid a 1/f noise detection is put into a region which is spectrally less noise-susceptible by the CARS wavelength being shifted by 40 kHz in relation to the OPO wavelength.

The detector 19 can be either a photomultiplier (PMT), a photodiode (PD) or an avalanche photodiode (APD). APDs are generally used in a counting mode for photons and generate an electronic pulse for each detected photon. The photomultiplier and the photodiode are connected to a transimpedance amplifier which at 0 ohms is terminated by an operational amplifier (OPAMP), as is shown by the insert in FIG. 2. The photodiode PD can be viewed as a current source, with a current proportional to the detected intensity (typically 0.6 A/W). The dominant noise sources in the detector are Johnson noise in the resistor ($\sqrt{(4\,kTR \cdot BW)}$, wherein BW represents the detection bandwidth in HZ, the amplifier current noise (dark current independently of R) and the shot noise of the number of electrons which are generated by the detected signal. The detected voltage scales linearly with the transimpedance resistor (R). By increasing the resistance to a point where it dominates over the other noise sources, the signal-to-noise ratio of the amplifier scales with A/R and for a sufficiently great output the noise is dominated by the shot noise of the detected signal. The maximum of R is limited by the required bandwidth of the amplifier, which scales with 1/R. A typical configuration attains a 1 MHz bandwidth for 1 MΩ transimpedance. The photomultiplier PMT is designed similarly to the photodiode PD, except that the dark current is less if it is compared to a resistor of similar gain. With a gain of $10^7$ a photomultiplier typically has 100 photons×BW dark count rate noise (10 kilo/s dark counter). Avalanche photodiodes APD have the lowest dark count rate (approximately 10 photons×BW).

If the amount of power of the local oscillator strength LO, 9 is increased at the detector, the noise (signal without any CARS signal at the detector) firstly presents the dark count noise level (flat), followed by a portion showing the shot noise of the local oscillator field. That is shown as a gradient ½ in a double-logarithmic representation in relation to the LO power (parallel to the line A in FIG. 2). At a given point the noise is dominated by the amplitude fluctuation of the local oscillator field LO, 9. The amplitude fluctuations are correlated with the power of the local oscillator LO, 9 and therefore scale with a gradient of 1 (parallel to the line B). As that portion of the noise scales more quickly than the heterodyne signal 4 (the latter scales in parallel with the line A) the signal-to-noise ratio drops. The window in which CARS signals can be detected only limitedly due to the shot noise rises where the noise follows the line A. The window is definingly closed by the noise caused by the amplitude fluctuations.

The amplification dynamics in the OPO determine the amplitude fluctuations, in particular the saturation level. If the OPO is not greatly saturated the amplitude fluctuations can occur at a (local oscillator) level where the noise is not yet dominated by the shot noise and effectively close the window for shot noise-limited detection.

Figure 4:
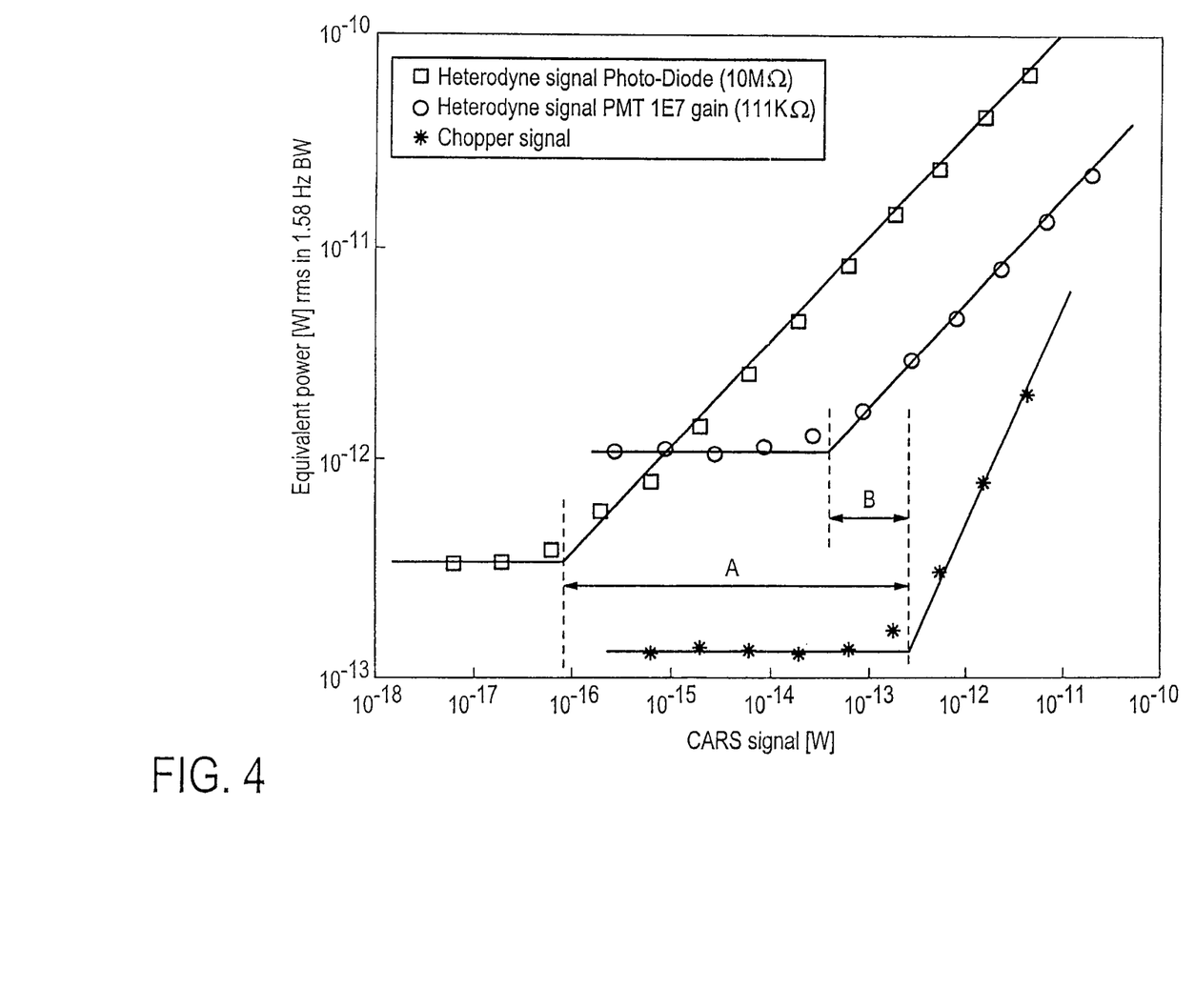
FIG. 4 shows a graph relating to the comparison of a heterodyne-detected non-linear optical signal in relation to a directly detected signal plotted in relation to a CARS power; view (A) represents an improvement factor (in the present case 3500) of a detection sensitivity between heterodyne detection and direct detection (for example with a chopper and a lock-in technology) of a non-linear signal on a photodiode; and view (B) represents the improvement factor (in the present case 7.5) for detection with a photomultiplier.

The level of the detected shot noise in comparison with the real optical shot noise scales inversely with the root of quantum efficiency (QE), which shifts the part of the line upwards. The position of the amplitude fluctuations remains unaffected and scales directly with the number of photons. That seems to improve the detection window insofar as higher levels of a local oscillator field LO, 9 are allowed, but in reality the level of detection sensitivity is worsened, as FIG. 4 shows. Photomultipliers have a tendency to have a low quantum efficiency (QE between 10% and 0.1%) for wavelengths near the near infrared (NIR). Photodiodes and avalanche photodiodes have a very much better quantum efficiency (QE typically up to 85%). For the detection of very small signals therefore avalanche photodiodes have proven to be the comparatively best choice. For practical applications photodiodes can be favored because they are large, inexpensive and robust. Avalanche photodiodes are comparatively costly and fragile and have a comparatively reduced dynamic range. As long as a window in which shot noise-limited detection is possible exists the choice of the detector is comparatively uncritical. The situation is different however if the window becomes comparatively small due to a process as described hereinbefore.

In the present case the wavelength of the IPO idler beam 8 is tuned to 1578 nm so that the differential frequency between the 1064 nm of the first beam 3 and the 1578 nm of the idler beam 9 coincides with a C-H stretch vibration excitation at 3060 cm$^{-1}$ in toluene. The OPO signal 9 (like the CARS signal) is at a wavelength of 802.7 nm. The toluene sample (material 16) is prepared between cover glasses and is about 15 µm in thickness. Some ten milliwatts at 1064 nm and 1578 nm are focused using a 0.60 NA air objective 13.1. The CARS signal is focused with a 0.65 NA objective 13.2. The filters 13.3 remove the 1578 nm and 1064 nm components of the excitation fields 3, 8.

To shift the CARS frequency an acousto-optical modulator 14 AOM is used, which is placed in the 1064 nm first beam 3 rather than in the signal beam 9 because its wavelength is not changed in the course of further tuning of the OPO to a given vibronic frequency. The AOM is operated at 80 MHz and effectively shifts the 1064 nm pulse at a repetition rate of 80.02 MHz by 20 kHz. That shift is converted into a shift of 40 kHz at the CARS wavelength by virtue of the involvement of two protons of 1064 nm in the first beam 3 in the excitation process. The CARS wavelength (CARS) is combined at a detector 19 (PD, APD, PMT) with the OPO signal (LO), 9 at the above-mentioned wavelength to give the interference signal 4 and the detected intensity is passed to a lock-in amplifier 15 adjusted for detection at 40 kHz. An integration unit of 100 ms, using a second-order edge filter (BW=1.58 Hz) is used.

Figure 2:
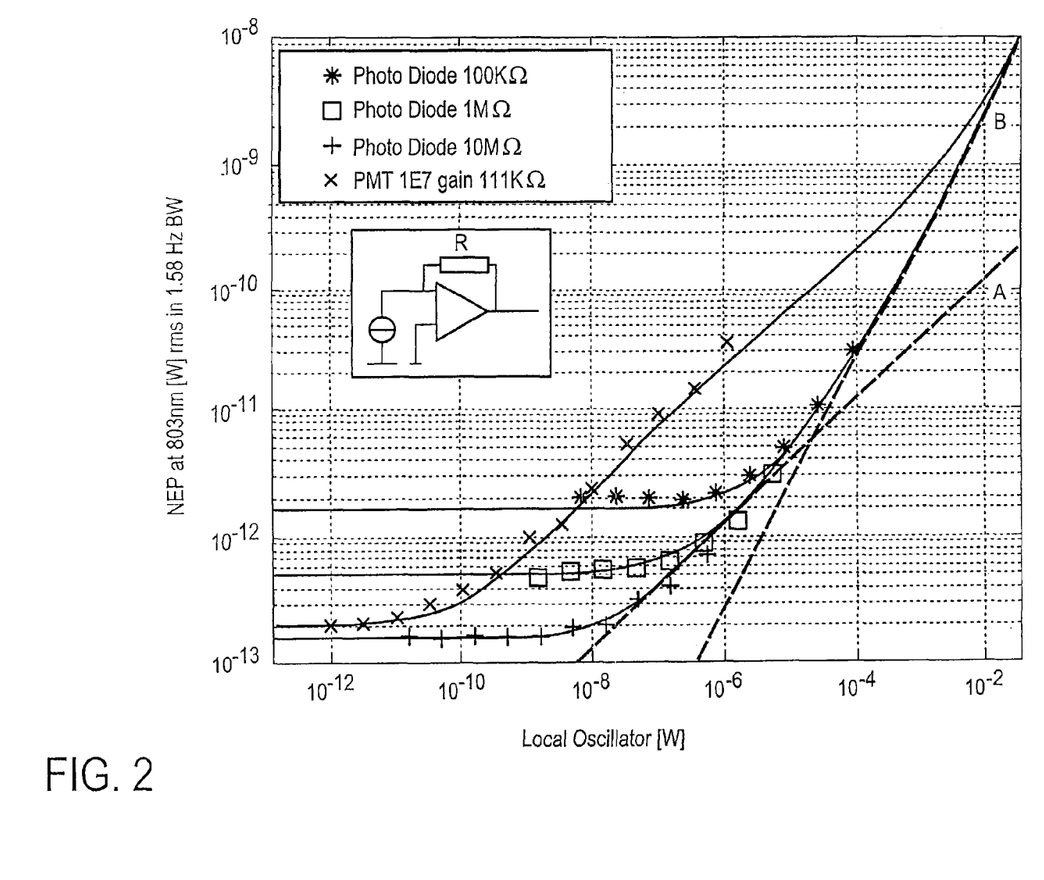
FIG. 2 shows the noise for different detectors as a function of a local oscillator strength, that is to say the signal beam or the signal pulse, wherein the broken lines A and B respectively represent a gradient of and 1 and the continuous lines represent a simulation, wherein the symbols represent measured data—the insert shows associated detector electronics.

FIG. 2 shows the detected noise levels for a photodiode with three different transimpedances and a photomultiplier as a function of a power of the local oscillator field LO. The noise levels are calculated back to a noise-equivalent input power (at 803 nm, 1.58 Hz bandwidth) as a comparison. The shot noise line for the photomultiplier is markedly above that for photodiodes by virtue of the low quantum efficiency (QE=0.3%). The photomultiplier exhibits a large window for shot noise-limited detection. The photodiodes have a window, only if they are set at 1 mΩ or 10 mΩ. At a lower setting the required local oscillator field LO introduces noise levels of noise dominated by amplitude fluctuation. Above 10 mΩ it is no longer possible for the OPAMP to follow the 40 kHz oscillations in accordance with the gain.

Figure 3:
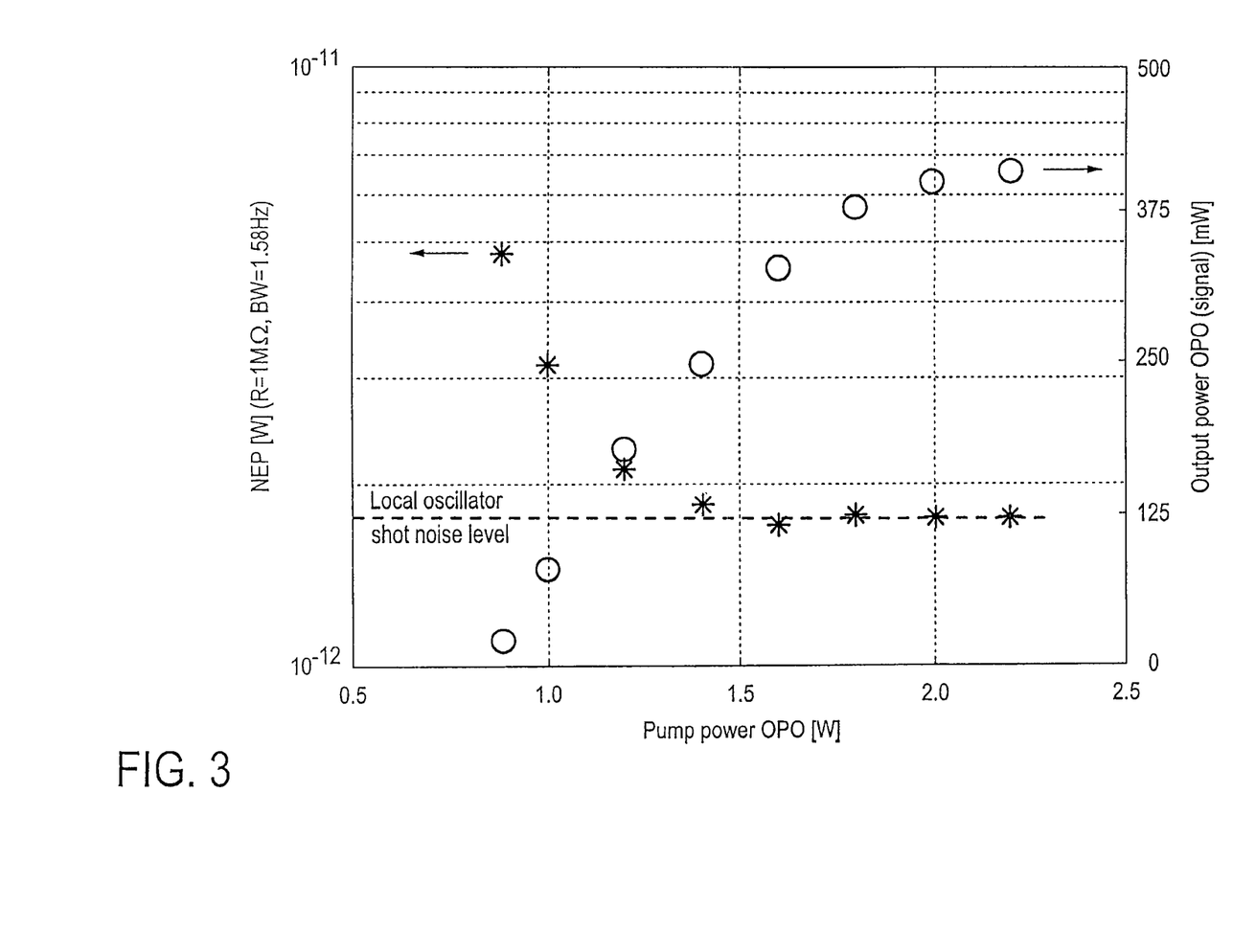
FIG. 3 shows the noise for a non-linear optical signal with 2 microwatt power and the total signal yield plotted against a pump power for the optical parametric oscillator (at 532 nm within the crystal)

The dependency of the amplitude fluctuation levels on the saturation of the OPO is demonstrated in FIG. 3 where both the power of the signal 9 at the output of the OPO and also the detected noise at the heterodyne frequency for a fixed level of the local oscillator field LO at the detector (2 µmW) is shown. Pumping of the OPO at 5 W and 532 nm instead of 2 W and 532 nm increases saturation. The reduction in the amplitude fluctuations permits shot noise-limited detection at lower transimpedance (and correspondingly higher frequency) until the input voltage noise dominates over the Johnson noise (below 50 kΩ).

In a modification in particular the use of an LBO-OPO which has a higher saturation level has proven to be advantageous. Modern pump sources for the OPO, with suitably short pulses, can permit a limit power at the OPO output at about 400 mW or more. Then saturation can be reached at three or four times the limit power, for example at between 1 watt and 1.5 watt power at the OPO output.

FIG. 4 shows a measured non-linear signal 17 as a heterodyne CARS signal at a fixed local oscillator level (50 nW for the photodiode and 2 nW for the photomultiplier), wherein the CARS signal (CARS) is varied by introducing attenuation filters 13.3 in the corresponding part of the beam. For comparison the drawing also shows the direct detection of the CARS signal with a removed local oscillator field (LO, 9), wherein instead the CARS signal of the non-linear signal is chopped with a mechanical chopper. The chopped signal shows the expected direct dependency on the CARS level with the gradient 1. The heterodyne signal 4 depends only on the root of the CARS signal and thus decreases with a gradient of ½. With increasing attenuation of the CARS level the directly detected signal disappears in the detector noise while heterodyne detection is continued at lower levels before it disappears in the local oscillator noise. For detection with a photodiode tuned at 10 MΩ the minimally detectable CARS signal, using heterodyne detection, is below the signal which can be directly detected by a factor of 3500. The photomultiplier has a very low noise level and a high gain so that this improvement due to heterodyne detection is not so impressive but nonetheless is at a factor of 7.5. It will be noted however that usually a quantum efficiency (QE) of the photomultiplier is comparatively low so that the minimum of a detectable signal is markedly above that which can be detected by heterodyne detection using a photodiode. There are photomultipliers with a quantum efficiency of up to 15%. For such photomultipliers, the heterodyne detection minimum would reach the limit of the photodiode. By virtue of remaining compensating errors such a detected heterodyne signal is below the theoretical limit by a factor of 10.

Noise-free heterodyne amplification is achieved for a level of the local oscillator (LO) which is so selected that the local oscillator noise is only a little above the detector dark noise level. In practice that means that comparatively low levels (nW) of the local oscillator LO are required to lift the signal above the detector noise, in comparison with light levels which drive the CARS signal (mW). In a modification the local oscillator (LO) can therefore be sent in colinear configuration with the other beams 3, 8 through a material sample without disturbing the CARS process, which advantageously avoids transit time differences in regard to a scanning microscopy operation.

The advantage of heterodyne detection is lower for an avalanche diode as the noise levels are lower and quantum efficiency is higher. It is important to establish however that the current detection limit is not caused solely by the detection noise. For a very small number of resonant molecules in the focus volume the non-resonant background can exceed the resonant signal, similarly to the way in which auto-fluorescence limits the detection of a fluorescence sample. The article referred to in the opening part of this specification by Potma et al shows that—as the resonant signal component in the phase is displaced in comparison with the non-resonant signal component—the interferometric signal can be used to separate the resonant components of the CARS signal from the non-resonant components and to suppress that background. In order also to avoid noise amplification of the non-resonant signal the polarisation directions of the incident beams 3, 8 and the local oscillator can be adapted to each other in order to amplify only the resonant part of the CARS signal in accordance with optical interference. The total loss of signal is compensated by the interferometric amplification effect and the noise generated by the non-resonant component is not added to the noise of the resonant component. Such a combination of heterodyne interference and a polarisation CARS detection system (HIPCARS) is also found to be advantageous.

To sum up the possibility of noise-free amplification for a non-linear signal (CARS) in the form of a CARS signal was demonstrated by way of example, which makes the OPO more advantageous for implementation of an optical structure 10 in a multi-beam configuration for heterodyne detection, this preferably being in comparison with the solutions set out in the opening part of this specification—which for example use a non-linear glass fiber or a reference CARS structure with a d-DMSO sample or another material with high Chi (3) and in which the noise levels are completely unspecified. In addition with the optical structure 10 by way of example illustrated herein there is an inherently temporal jitter-free operating option so that it is possible to effect a wavelength scan without synchronisation errors and there is the possibility of separating resonant and non-resonant components. That will significantly improve the usability of an apparatus of the kind discussed in the context of CARS microscopy.

The invention concerns a method and an optical arrangement 10 for generating a non-linear optical signal (CARS) on a material excited by an excitation field 2, wherein coherent fields of optical pulses of differing frequency are overlapped in the material in temporal and spatial relationship with the excitation field 2, wherein first pulses of a first frequency are generated in a first beam 3 of a first optical generator unit 2 and second pulses of a second frequency are generated in a second beam 8 of a second optical generator unit 7 synchronously pumped by the first optical generator unit 1. In accordance with the concept of the invention the method provides that with the pulses of the first frequency as the fundamental frequency (1064 nm) pulses of a higher harmonic frequency (532 nm) thereof are generated and the second optical generator unit 7 is pumped with the pulses at the higher harmonic frequency and the second optical generator unit 7 as an optical parametric generator unit generates pulses of an idler frequency (1578 nm) in an idler beam for producing the second pulses of the second frequency in the second beam 8, wherein the second frequency (1578 nm) is smaller than the first frequency (1064 nm) and the second optical generator unit 7 generates pulses of a signal frequency (802.7 nm) in a signal beam 9, wherein the second frequency (1578 nm) is smaller than the signal frequency (802.7 nm).

The invention claimed is:

1. A method of generating a non-linear optical signal (17) on a material (16) excited by an excitation field (2), wherein with the excitation field (2) coherent fields of first and second optical pulses of differing frequency are overlapped in the material (16) in temporal and spatial relationship, wherein
the first pulses of a first frequency are generated in a first beam (3) of a first optical generator unit (1), and
the second pulses of a second frequency are generated in a second beam (8) of a second optical generator unit (7) synchronously pumped by the first optical generator unit (1),
wherein with the first pulses of the first frequency as a fundamental frequency pulses of a higher harmonic frequency thereof are generated (SHG) and the second optical generator unit is pumped with the pulses (5) of the higher harmonic frequency,
and wherein the second optical generator unit (7) as an optical parametric generator unit generates pulses of an idler frequency in an idler beam for providing the second pulses of the second frequency in the second beam (8), wherein the second frequency is smaller than the first frequency, and
the second optical generator unit (7) generates pulses of a signal frequency in a signal beam (9), wherein the second frequency is smaller than the signal frequency, and wherein the non-linear optical signal (17) is overlapped for detection heterodynely in interfering relationship with the signal beam (9).

2. A method as set forth in claim 1, wherein the sum of the idler frequency and the signal frequency corresponds to the higher harmonic frequency.

3. A method as set forth in claim 2, wherein the sum of the idler frequency and the signal frequency corresponds to the frequency of a second harmonic.

4. A method as set forth in claim 1, wherein the non-linear optical signal (17) is formed at a frequency which corresponds to double the first frequency minus the idler frequency.

5. A method as set forth in claim 4 wherein the non-linear optical signal (17) is in the form of a CARS signal.

6. A method as set forth in claim 1, wherein an optical phase position is defined between a pulse of the signal beam (9) and the non-linear optical signal (17).

7. A method as set forth in claim 6, wherein a phase position is undefined between a pulse of the first beam (3) and a pulse of the second beam (8).

8. A method as set forth in claim 1, wherein the signal frequency and the frequency of the non-linear optical signal (17) coincide in their order of magnitude.

9. A method as set forth in claim 1, wherein a frequency of the non-linear optical signal (17) alters relative to the signal frequency of the signal beam (9) and the non-linear optical signal (17) is detected by way of a time-dependent interfering signal (4).

10. A method as set forth in claim 1, wherein a frequency and/or phase of the non-linear optical signal (17) is altered relative to the signal frequency and/or phase by the first frequency and/or phase being altered.

11. A method as set forth in claim 10, wherein the first frequency and/or phase is altered by a frequency-modulating and/or phase-modulating means.

12. A method as set forth in claim 1, wherein the first beam (3) and the second beam (8) are collinearly overlapped.

13. A method as set forth in claim 1, wherein the signal beam (9) or a part thereof is collinearly overlapped with the non-linear optical signal (17).

14. A method as set forth in claim 13, wherein the signal beam (9) or a part thereof is collinearly overlapped with non-linear optical signal (17) in a detector (19).

15. A method as set forth in claim 1, wherein the signal beam (9) or a part thereof is collinearly overlapped with the first beam (3) and the second beam (8).

16. A method as set forth in claim 15, wherein the signal beam (9) or a part thereof is collinearly overlapped with the first beam (3) and the second beam (8) in the material (16).

17. A method as set forth in claim 1, wherein the intensity of the signal beam (9) is selected to be low such that a strength of the non-linear optical signal (17) is uninfluenced by the signal beam (9).

18. A method as set forth in claim 1, wherein the intensity of the signal beam (9) is selected to be high such that a strength of the non-linear optical signal (17) rises with the intensity of the signal beam (9).

19. A method as set forth in claim 1, wherein the fields of the first beam (3) and the second beam (8) are copolarised or non-copolarised, or are so selected that the excitation field (2) is circularly or elliptically polarised.

20. A method as set forth in claim 19, wherein the fields of the first beam (3) and the second beam (8) are cross-polarised.

21. Use of a method as set forth in claim 1 for the chemically selective investigation of chemical substances and/or biological substances.

22. Use of a method as set forth in claim 1 for the chemically selective investigation of chemical substances and/or biological substances in the foodstuffs sector.

23. Use of a method as set forth in claim 1 for the investigation of vibronic states in a molecule.

24. Use of a method as set forth in claim 22, for the investigation of vibronic states in a molecule in relation to substances with a sub-milli-molar concentration of the molecule.

25. Use of a method as set forth in claim 1 for microscopy and/or spectroscopy.

26. Use of a method as set forth in claim 24 for CARS microscopy and/or CARS spectroscopy.

27. Use of a method as set forth in claim 1 for frequency metrology.

28. Use of a method as set forth in claim 25 for frequency metrology having phase-stabilized optical generator units (1, 7).

29. An optical arrangement (10) for generating a non-linear optical signal (17) on a material (16) excited by an excitation field (2), wherein with the excitation field (2) coherent first and second fields of optical pulses of differing frequency are overlapped in the material (16) in temporal and spatial relationship, comprising:
 a first optical generator unit (1) for generating the first pulses of a first frequency in a first beam (3),
 a means (18) for generating pulses (5) of a higher harmonic frequency with the first pulses of the first frequency as a fundamental frequency,
 a second optical generator unit (7) which is pumpable by the first optical generator unit (1) synchronously with the pulses (5) of the higher harmonic frequency and which is in the form of an optical parametric generator unit for generating pulses of an idler frequency in an idler beam as second pulses in the second beam (8) at a second frequency and for generating pulses of a signal frequency in a signal beam (9), wherein the second frequency is smaller than the first frequency and smaller than the signal frequency, and
 beam guide means (11) for temporal and spatial overlapping of a first pulse of the first beam and a second pulse of the idler beam, and
 further beam guide means (12) adapted for detection of the non-linear optical signal (17) by heterodyne interfering overlapping with the signal beam (9).

30. An optical arrangement as set forth in claim 29, further comprising a means (14) for altering the frequency of the non-linear optical signal relative to the signal frequency of the signal beam, and
 a detector (19) and further beam guide means (12) for heterodyne interfering overlapping of the non-linear optical signal (17) with the signal beam (9) in the detector (PD, APD, PMT).

31. An optical arrangement as set forth in claim 29 wherein the first optical generator unit (1) is formed in the form of a laser.

32. An optical arrangement as set forth in claim 31, wherein the first optical generator unit (1) is formed in the form of an Nd:YAG or a Ti: sapphire laser.

33. An optical arrangement as set forth in claim 29, wherein the second optical generator unit (7) is in the form of an optical parametric oscillator.

34. An optical arrangement as set forth in claim 33, wherein the second optical generator unit (7) is in the form of a KTP-OPO or LBO-OPO.

35. An optical arrangement as set forth in claim 29 wherein the second optical generator unit (7) is in the form of an optical parametric generator or an optical parametric amplifier.

36. An optical arrangement as set forth in claim 29, wherein the optical generator units (1, 7) are adapted to generate picosecond pulses.

37. An optical arrangement as set forth in claim 29, wherein the optical generator units (1, 7) are adapted to generate femtosecond pulses.

38. An optical arrangement as set forth in claim 29, wherein the means (18) for generating pulses of a higher harmonic frequency is in the form of a frequency doubler.

39. An optical arrangement as set forth in claim 38, wherein the means (18) for generating pulses of a higher harmonic frequency is in the form of a frequency doubler with one or more non-linear crystals.

40. An optical arrangement as set forth in claim 29, wherein the means for generating a higher harmonic frequency is arranged between the first optical generator unit (1) and the second optical generator unit (7).

41. An optical arrangement as set forth in claim 29, wherein the means for generating a higher harmonic frequency is formed in a resonator of the first optical generator unit.

42. An optical arrangement as set forth in claim 29, wherein a means (14) for altering the frequency and/or phase of the non-linear optical signal relative to the frequency and/or phase of the signal beam is arranged as a means for altering the fundamental frequency and/or phase in the first beam (3) and/or the idler frequency and/or phase in the idler beam (8) and/or the signal frequency and/or phase in the signal beam (9).

43. An optical arrangement as set forth in claim 42, wherein the means is in the form of an acousto-optical modulator (AOM).

44. An optical arrangement as set forth in claim 29, wherein the detector (19) is in the form of a photomultiplier (PMT), a photodiode (PD) or an avalanche diode (APD).

* * * * *